(12) United States Patent
Chang et al.

(10) Patent No.: US 10,693,053 B2
(45) Date of Patent: Jun. 23, 2020

(54) METHOD FOR PRODUCING INTRAVASCULAR ULTRASONIC TRANSDUCERS AND STRUCTURE THEREOF

(71) Applicant: SOGANG UNIVERSITY RESEARCH FOUNDATION, Seoul (KR)

(72) Inventors: Jin Ho Chang, Seoul (KR); Tai-Kyong Song, Seoul (KR); Yang Mo Yoo, Gyeonggi-do (KR); Junsu Lee, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 525 days.

(21) Appl. No.: 15/114,712

(22) PCT Filed: Jan. 28, 2015

(86) PCT No.: PCT/KR2015/000866
§ 371 (c)(1),
(2) Date: Jul. 27, 2016

(87) PCT Pub. No.: WO2015/115779
PCT Pub. Date: Aug. 6, 2015

(65) Prior Publication Data
US 2016/0351783 A1 Dec. 1, 2016

(30) Foreign Application Priority Data

Jan. 29, 2014 (KR) .................. 10-2014-0011682
Jan. 29, 2014 (KR) .................. 10-2014-0011683

(51) Int. Cl.
*H01L 41/083* (2006.01)
*H01L 41/337* (2013.01)
(Continued)

(52) U.S. Cl.
CPC .............. *H01L 41/083* (2013.01); *A61B 8/12* (2013.01); *B06B 1/0648* (2013.01); *H01L 41/27* (2013.01);
(Continued)

(58) Field of Classification Search
CPC ......... H01L 41/083; H01L 41/27; A61B 8/12; A61B 8/0891; B06B 1/0648
See application file for complete search history.

(56) References Cited

U.S. PATENT DOCUMENTS 5,271,402 A * 12/1993 Yeung ................. A61B 8/12
600/437
5,406,951 A 4/1995 ten Hoff et al.
(Continued)

FOREIGN PATENT DOCUMENTS

JP 06-225391 8/1994
JP 07-299071 11/1995
(Continued)

*Primary Examiner* — Bryan P Gordon
(74) *Attorney, Agent, or Firm* — Duane Morris LLP; J. Rodman Steele, Jr.; Gregory M. Lefkowitz (57) ABSTRACT

The present invention relates to a method for producing an intravascular ultrasonic transducer and a structure for same, the method for producing a ultrasonic transducer producing a single element by: forming a piezoelectric element lapped according to a previously set thickness; depositing conductive material on the lapped surface of the piezoelectric element; forming a matched layer and a rear surface layer by casting the front and rear surfaces of the piezoelectric element to which conductive material has been deposited; lapping according to a previously set thickness; and dicing the bulk material, which is a stack of a matched layer, a piezoelectric element and a rear surface layer, along the stack direction so that the size of the element is less than the critical size for intravascular ultrasound (IVUS).

19 Claims, 8 Drawing Sheets

(51) Int. Cl.
*A61B 8/12* (2006.01)
*B06B 1/06* (2006.01)
*H01L 41/27* (2013.01)
*H01L 41/35* (2013.01)
*A61B 8/08* (2006.01)
*A61B 8/00* (2006.01)

(52) U.S. Cl.
CPC ............ *H01L 41/337* (2013.01); *H01L 41/35* (2013.01); *A61B 8/0891* (2013.01); *A61B 8/4483* (2013.01)

(56) References Cited

U.S. PATENT DOCUMENTS

| | | |
|---|---|---|
| 5,546,948 A | 8/1996 | Hamm et al. |
| 6,019,727 A | 2/2000 | Koger et al. |
| 6,124,664 A | 9/2000 | Mamayek et al. |
| 6,162,178 A | 12/2000 | Garcia et al. |
| 6,186,952 B1 | 2/2001 | White et al. |
| 2005/0085730 A1 | 4/2005 | Flesch et al. |
| 2007/0182290 A1 | 8/2007 | Guo et al. |
| 2008/0161696 A1* | 7/2008 | Schmitt ................ A61B 5/0066 600/467 |
| 2009/0062656 A1* | 3/2009 | Hyuga .................... A61B 8/12 600/459 |
| 2009/0171216 A1 | 7/2009 | Sadaka |
| 2011/0316389 A1* | 12/2011 | Kwon ................... B06B 1/0622 310/335 |
| 2014/0107491 A1* | 4/2014 | Fearnot ................ A61B 8/4461 600/463 |
| 2015/0297182 A1* | 10/2015 | Peng ..................... G01S 15/894 600/467 |
| 2016/0022244 A1* | 1/2016 | Courtney .......... A61M 25/0045 600/466 |

FOREIGN PATENT DOCUMENTS

| | | |
|---|---|---|
| JP | 07-312799 | 11/1995 |
| JP | 2012-143615 | 8/2012 |

* cited by examiner

METHOD FOR PRODUCING INTRAVASCULAR ULTRASONIC TRANSDUCERS AND STRUCTURE THEREOF

CROSS-REFERENCE TO RELATED APPLICATIONS

This application is a § 371 national stage entry of International Application No. PCT/KR2015/000866, filed Jan. 28, 2015, which claims priority to South Korean Patent Application No. 10-2014-0011682, filed on Jan. 29, 2014, and South Korean Patent Application No. 10-2014-0011683, filed on Jan. 29, 2014, the entire contents of which are incorporated herein by reference.

TECHNICAL FIELD

The present disclosure relates to an ultrasonic transducer for medical imaging, and more particularly, a method for producing a high frequency transducer which is a core element in intravascular ultrasonic imaging and an intravascular ultrasonic transducer structure according to the method.

BACKGROUND ART

Ultrasound (US) imaging is equipment for imaging the structure and characteristics of an observation region in the human body by applying an ultrasonic signal to the observation region using an ultrasonic probe, receiving the ultrasonic signal reflected back from the tissue, and extracting information included in the signal. Its advantage is that real-time images with no adverse effect on the human body can be obtained at low costs, when compared to other medical imaging systems such as X-ray, CT, MRI, and PET.

On the other hand, intravascular ultrasound (IVUS) imaging technology refers to image processing technology and scheme for the real-time cross-sectional imaging of arteria in blood vessels or visualization of diseases occurred in blood vessels, and population aging and increasing number of people with chronic diseases such as cardiac diseases supports market growth, and low-cost treatments are required all over the world. Under this circumstance, IVUS can cope with the requirements that have been impossible to meet so far in early discovery and prevention of coronary artery diseases, and it has very high potential. Furthermore, as revealed from some international clinical research, this technology has more advantages than existing angiography, so it becomes popular. The use of IVUS for left main diseases, chronic complete obstruction, lower limb peripheral arterial diseases, and induction of blood vessel formation is a major challenging field of this technology.

For IVUS imaging, a core element, namely, a high frequency transducer needs to be produced with proper efficiency and costs. Because IVUS creates visual representations by inserting a transducer into the blood vessel, the diameter of the transducer should be 1 mm or less, and frequencies used to obtain high resolution images are high frequencies in 20-100 MHz bands. Because an IVUS transducer with small size, ability to transmit and receive ultrasound waves of high frequencies and disposability should be produced at a low cost, an efficient and economical production method is a key technical obstacle of IVUS imaging equipment. Prior Art Reference presented below describes an array ultrasonic transducer for IVUS imaging.

PRIOR ART REFERENCE

Development of circular array ultrasonic transducer, Heewon Kim, Yongrae Roh, Acoustical Society of Korea in 2002, Proceedings of Summer meeting of the Acoustical Society of Korea Vol. 21 No. 1

DISCLOSURE

Technical Problem

The technical problem to be solved by the embodiments of the present disclosure is to overcome the limitation that it is impossible to provide an effective and economical yield in producing an ultrasonic transducer for IVUS with a high operating frequency, a very thin material of each component, and a very small aperture size enough that it can be inserted into the blood vessel, and to solve the problem which is an inability to achieve transducer characteristics desired by consumers due to the use of an adhesive in producing an ultrasonic transducer, and a failure to accomplish desired beam convergence due to natural focusing.

Technical Solution

To solve the technical problem, a method for producing an ultrasonic transducer according to an embodiment of the present disclosure includes forming a piezoelectric material lapped according to a preset thickness, depositing a conductive material on a lapped surface of the piezoelectric material, casting a front surface and a rear surface of the piezoelectric material having the deposited conductive material to respectively form a matching layer and a backing layer and lapping according to a preset thickness, and dicing the bulk material with a stack of the matching layer, the piezoelectric material and the backing layer along a stack direction to produce single elements which are less than or equal to a threshold size for intravascular ultrasound (IVUS).

In the method for producing an ultrasonic transducer according to an embodiment, the matching layer and the backing layer may be formed directly on the conductive material through the casting without using an adhesive material. Further, in the method for producing an ultrasonic transducer according to an embodiment, the matching layer and the backing layer may be cured using a centrifugal separator after the casting.

To solve the technical problem, an ultrasonic transducer structure according to another embodiment of the present disclosure includes a tube for insertion into a blood vessel for IVUS, an ultrasonic transducer of a single element consisting of a stack of a matching layer, a piezoelectric material and a backing layer, and installed at an end of the tube to obtain an ultrasonic image, and a support positioned between one side wall of the tube and the ultrasonic transducer to form an angle at which the ultrasonic transducer is oriented, and to adjust the angle to make an ultrasonic radiation angle of the ultrasonic transducer different from an insertion angle of the tube.

In the ultrasonic transducer structure according to another embodiment, the ultrasonic transducer is produced as a single element by forming a piezoelectric material lapped according to a preset thickness, depositing a conductive material on a lapped surface of the piezoelectric material, casting a front surface and a rear surface of the piezoelectric material having the deposited conductive material to respectively form a matching layer and a backing layer and lapping according to a preset thickness, and dicing the bulk material with a stack of the matching layer, the piezoelectric material and the backing layer along a stack direction to allow insertion into the tube.

In the ultrasonic transducer structure according to another embodiment, the angle at which the ultrasonic transducer is oriented by the support may be determined to range between 0° and 90° from an insertion direction of the tube, to simultaneously obtain ultrasonic images of the insertion direction of the tube and a wall surface of the blood vessel into which the tube is inserted, or to estimate a Doppler frequency and calculate a blood flow velocity.

In the ultrasonic transducer structure according to another embodiment, the ultrasonic transducer may be formed in rectangular shape, a length of a short side of the ultrasonic transducer may be at least less than or equal to a diameter of the tube, and a length of a long side of the ultrasonic transducer may be larger than or equal to the diameter of the tube, and the long side of the ultrasonic transducer may be inserted along an inner wall surface of the tube.

In the ultrasonic transducer structure according to another embodiment, the end of the tube at which the ultrasonic transducer is installed may have a cutting plane forming a slant in consideration of the ultrasonic radiation direction of the ultrasonic transducer.

In the ultrasonic transducer structure according to another embodiment, the ultrasonic transducer may form a gradient such that a center surface is concave, to converge a beam to a geometrical focus of the ultrasonic transducer. Further, in the ultrasonic transducer structure according to another embodiment, the ultrasonic transducer may further include a convex lens attached to a front surface, to converge a beam to a geometrical focus of the ultrasonic transducer.

In the ultrasonic transducer structure according to another embodiment, the ultrasonic transducer may further include an optical source module which is inserted into a certain region of the ultrasonic transducer to emit an optical signal for photoacoustic imaging or optical coherence tomography (OCT) imaging.

In the ultrasonic transducer structure according to another embodiment, an electrical signal may be supplied to the backing layer, and ground may be created by connecting a housing to the matching layer.

In the ultrasonic transducer structure according to another embodiment, the ultrasonic transducer of a single element may consist of a sequential stack of the piezoelectric material, a first signal pad, a ground pad formed spaced apart from the first signal pad, a flexible printed circuit board (FPCB), and a second signal pad electrically connected to the first signal pad through a via penetrating the FPCB, the backing layer may be lapped according to a preset thickness and formed on a lower surface of the second signal pad, and after the matching layer electrically connects an upper surface of the piezoelectric material and the ground pad, the matching layer may be lapped according to a preset thickness and formed on the upper surface of the piezoelectric material.

Advantageous Effects

The embodiments of the present disclosure propose process technology for the simultaneous production of a plurality of individual single element IVUS ultrasonic transducers through dicing, thereby producing an ultrasonic transducer which has a high operating frequency and an ultramicro aperture size and ensures economical efficiency without an adhesive, and accomplishing beam convergence through a geometrical focus.

DETAILED DESCRIPTION OF MAIN ELEMENTS

10: Ultrasonic transducer
11: Piezoelectric material
13: Matching layer
15: Backing layer
17: Lens
19: Optical source module
20: Intravascular tube
30: Support
40: Wire
50: Housing
100: Ultrasonic transducer with stacked structure
101: Single element ultrasonic transducer
110: FPCB
111: First signal pad
112: Second signal pad
113: Ground pad
114: Piezoelectric material
115: Via

BEST MODE

Hereinafter, the basic idea employed by the embodiments of the present disclosure is first presented in brief, and then, specific technical means will be described in a sequential order.

As opposed to an array transducer which is difficult to achieve high frequency for IVUS, a single element transducer may be produced by a method that carries out lapping and dicing of each material for a necessary backing layer, piezoelectric material, and matching layer respectively to suit a desired size and thickness, and adhesion each using an adhesive. However, because an IVUS transducer has a small thickness of each material and is small in size, when a general method for producing a single element transducer is used, it is difficult to obtain transducer characteristics (ultra-micro size and high frequency) desired by customers. Particularly, because the thickness of each material is most important in achieving high frequency and an adhesive may be act as one layer, there is a risk of performance degradation of an IVUS transducer when produced according to the above-described process.

Accordingly, the embodiments of the present disclosure presented hereinafter are intended to propose efficient and economical process technology that makes each material of a backing layer, a piezoelectric material and a matching layer at a desired thickness first, and then, performs matching and dicing to produce a plurality of individual IVUS transducers at the same time.

As an embodiment of the present disclosure, there is provided a method for producing an ultrasonic transducer including: forming a piezoelectric material lapped according to a preset thickness; depositing a conductive material on the lapped surface of the piezoelectric material; casting a front surface and a rear surface of the piezoelectric material having the deposited conductive material to respectively form a matching layer and a backing layer and lapping according to a preset thickness; and dicing the bulk material with a stack of the matching layer, the piezoelectric material and the backing layer along the stack direction to produce single elements which are less than or equal to a threshold size for intravascular ultrasound (IVUS).

MODE FOR INVENTION

Hereinafter, preferred experiments are described in sufficient detail to enable those skilled in the art to easily practice the disclosure with reference to the accompanying drawing. However, it will be obvious to those skilled in the art that these embodiments are intended to describe the present disclosure in further detail, and the scope of the disclosure is not limited thereby.

Figure 1:
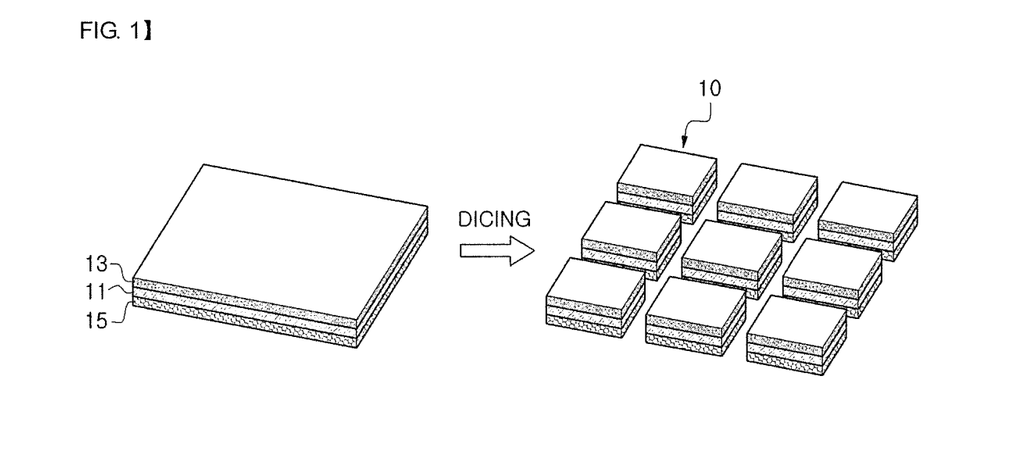
FIG. 1 is a conceptual diagram illustrating a process of producing an intravascular ultrasonic transducer employed by the embodiments of the present disclosure.

FIG. 1 is a conceptual diagram illustrating a process of producing an intravascular ultrasonic transducer employed by the embodiments of the present disclosure.

FIG. 1 shows a method for making a single element needed to produce an IVUS transducer, including making a piezoelectric material 11, a matching layer 13, and a backing layer 15 having a large size to suit a desired thickness, following by adhesion. In this instance, the matching layer 13 and backing layer 15 used may be made using a conductive material. Subsequently, the stacked element may be diced into a necessary size (for example, a size of at least less than or equal to 1 mm×1 mm is preferred) to produce a plurality of single elements 10.

Figure 2:
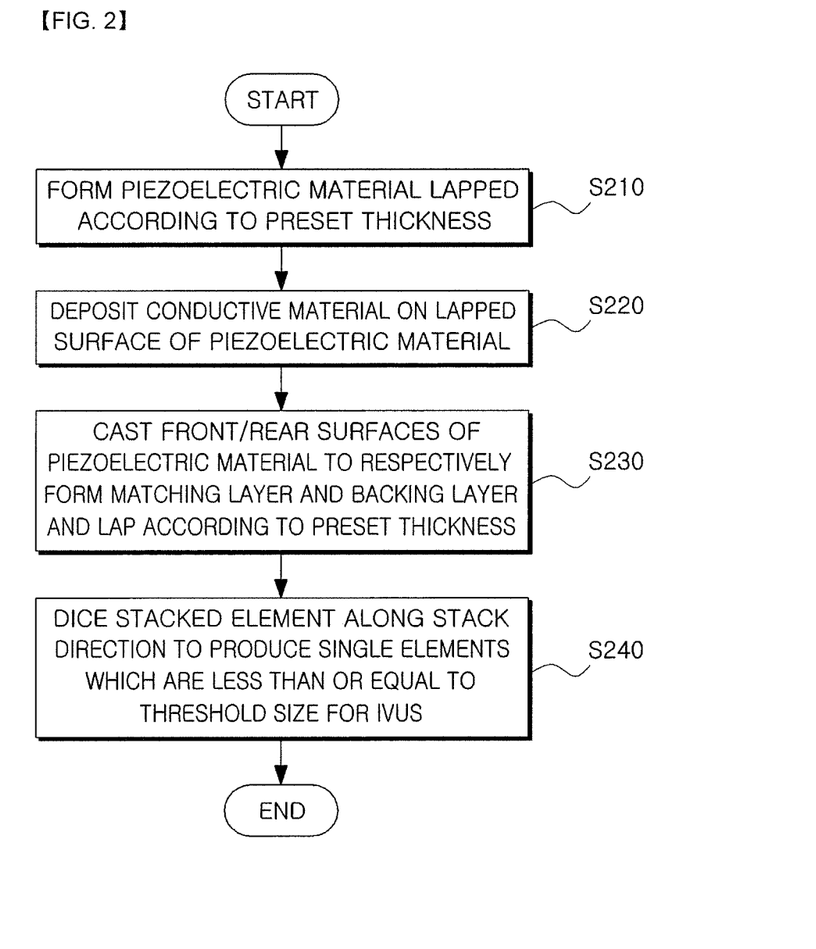
FIG. 2 is a flowchart showing a method for producing an intravascular ultrasonic transducer according to an embodiment of the present disclosure.

FIG. 2 is a flowchart showing a method for producing an intravascular ultrasonic transducer according to an embodiment of the present disclosure.

At S210, a piezoelectric material lapped according to a preset thickness is formed.

At S220, a conductive material is deposited on the lapped surface of the piezoelectric material formed through S210. For the conductive material, chrome or gold may be used, but is not limited thereto.

At S230, a front surface and a rear surface of the piezoelectric material having the deposited conductive material may be cast to form a matching layer and a backing layer, respectively, and may be lapped according to a preset thickness. The matching layer and the backing layer may be formed by curing using a centrifugal separator after casting. For example, curing may be induced for one day at room temperature.

Here, the matching layer and the backing layer are preferably formed directly on the conductive material through casting without using an adhesive material. Accordingly, in this embodiment, it is more advantageous for achieving high frequency characteristics because the problem with the use of an adhesive as described previously does not occur.

At S240, bulk material consisting of a stack of the matching layer, the piezoelectric material and the backing layer may be diced along the stack direction to produce single elements which are less than or equal to a threshold size for intravascular ultrasound (IVUS). For example, this threshold size may be determined to be less than or equal to 1 mm×1 mm that is at least smaller than the cross section of the blood vessel.

Figure 3:
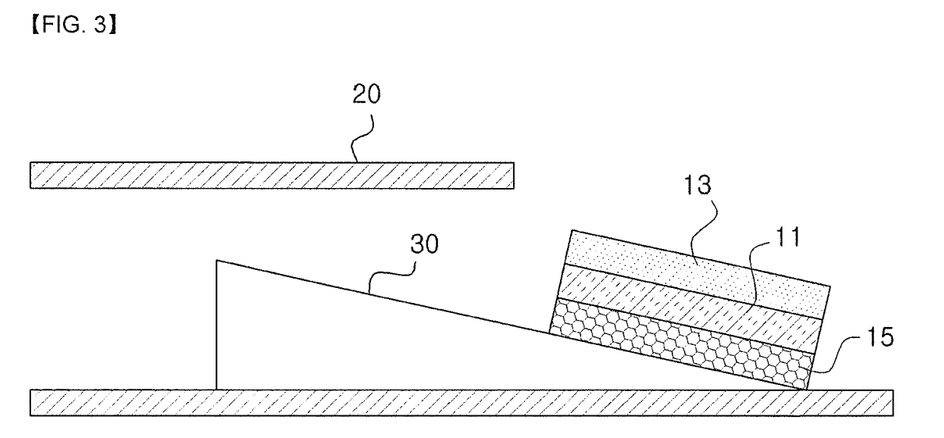
FIG. 3 is a cross-sectional view showing the structure of an intravascular ultrasonic transducer structure according to another embodiment of the present disclosure.

FIG. 3 is a cross-sectional view showing the structure of an intravascular ultrasonic transducer structure according to another embodiment of the present disclosure, largely including the ultrasonic transducer 10: 11, 13, 15, a support 30 and a tube 20.

The tube 20 is an outer body for intravascular IVUS.

The ultrasonic transducer 10 is a single element which consists of a stack of the matching layer 13, the piezoelectric material 11 and the backing layer 15 and is installed at the end of the tube 20 to obtain an ultrasonic image. The ultrasonic transducer 10 may be produced as a single element by forming the piezoelectric material 11 lapped according to a preset thickness, depositing a conductive material on the lapped surface of the piezoelectric material 11, casting a front surface and a rear surface of the piezoelectric material 11 having the deposited conductive material to respectively form the matching layer 13 and the backing layer 15 and lapping according to a preset thickness, and dicing bulk material consisting of a stack of the matching layer 13, the piezoelectric material 11 and the backing layer 15 along the stack direction to allow the insertion into the tube 20.

The support 30 is positioned between one side wall of the tube 20 and the ultrasonic transducer 10: 11, 13, 15 to form an angle at which the ultrasonic transducer 10: 11, 13, 15 is oriented, and acts as an adjuster to make an ultrasonic radiation angle of the ultrasonic transducer 10: 11, 13, 15 different from an insertion angle of the tube 20. That is, the support 30 may be embodied as a sort of pad which is fixed to the tube 20 to adjust the angle of the ultrasonic transducer 10: 11, 13, 15.

Here, the angle at which the ultrasonic transducer 10: 11, 13, 15 is oriented by the support 30 is determined to range between 0° and 90° from the insertion direction of the tube 20, inducing the simultaneous acquisition of ultrasonic images of the insertion direction of the tube 20 and the wall surface of the blood vessel into which the tube 20 is inserted. Through the support 30, the ultrasonic transducer structure according to this embodiment has an advantage; not only either the blood vessel wall surface or the front in the insertion direction of the tube can be observed but also both can be observed simultaneously. In addition, through the support 30, the ultrasonic transducer structure according to this embodiment may estimate a Doppler frequency and calculate a blood flow velocity.

Also, the end of the tube 20 at which the ultrasonic transducer 10: 11, 13, 15 is installed preferably has a cutting plane forming a slant in consideration of the ultrasonic radiation direction of the ultrasonic transducer.

On the other hand, the embodiment of the present disclosure presented through FIG. 3 is intended to use the properties of a tube in producing an ultrasonic transducer for beam convergence. An element used for an IVUS transducer has a size limited by the width of the blood vessel. However, the size in the depth-wise direction of the blood vessel is not limited. Thus, the element may be produced with a long size in the depth-wise direction of the blood vessel. To this end, preferably, the ultrasonic transducer 10: 11, 13, 15 is formed in rectangular shape, the length of the short side of the ultrasonic transducer 10: 11, 13, 15 is at least less than or equal to the diameter of the tube, the length of the long side of the ultrasonic transducer 10: 11, 13, 15 is larger than or equal to the diameter of the tube, and the long side of the ultrasonic transducer 10: 11, 13, 15 is inserted along the inner wall surface of the tube. Through this structure, the ultrasonic transducer can improve the resolution of an image through beam convergence.

Figure 4A:
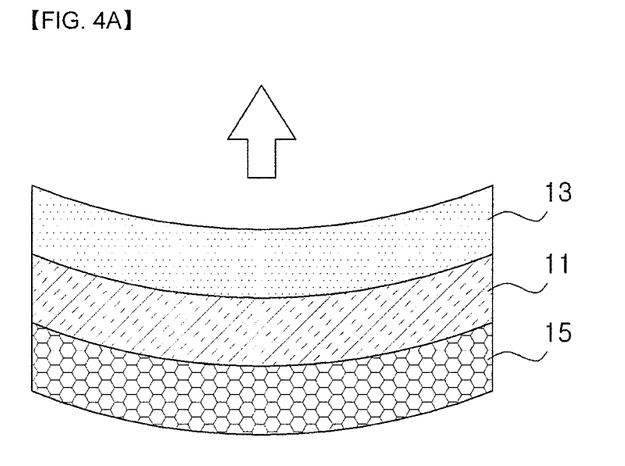
FIGS. 4A and 4B are diagrams illustrating a method for inducing beam convergence in the ultrasonic transducer structure of FIG. 3 according to another embodiment of the present disclosure.
Figure 4B:
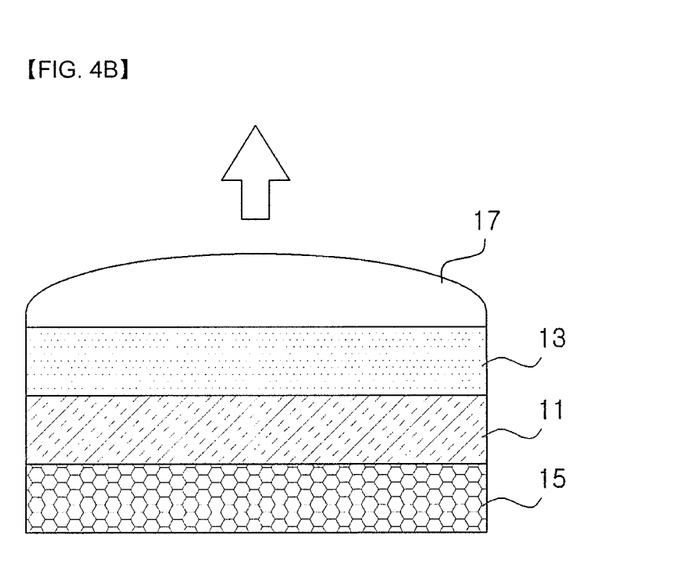

FIGS. 4A and 4B are diagrams showing an example of two methods for describing a method for inducing beam convergence in the ultrasonic transducer structure of FIG. 3 according to another embodiment of the present disclosure.

A general element used for a transducer in the blood vessel is produced in oval or square shape. That is, because the element is very small in size, natural focusing is created. A weak point of beam convergence using natural focusing is that it is impossible to converge to a point desired by a user and the convergence effect remarkably reduces. Thus, the method proposed in FIGS. 4A and 4B is producing the element in rectangular shape. Because the diameter size of the blood vessel is limited as described previously, it is possible to converge a beam even in one direction by producing the element with an increased size in the depth-wise direction of the blood vessel.

In FIG. 4A, the ultrasonic transducer 11, 13, 15 forms a gradient such that a center surface is concave, to converge a beam to a geometrical focus of the ultrasonic transducer. This can be realized by a method which forms a gradient in the rectangular element (ultrasonic transducer) using a heated iron bead.

In FIG. 4B, the ultrasonic transducer 11, 13, 15 further includes a convex lens 17 attached to the front surface, to converge a beam to the geometrical focus of the ultrasonic transducer.

Figure 5:
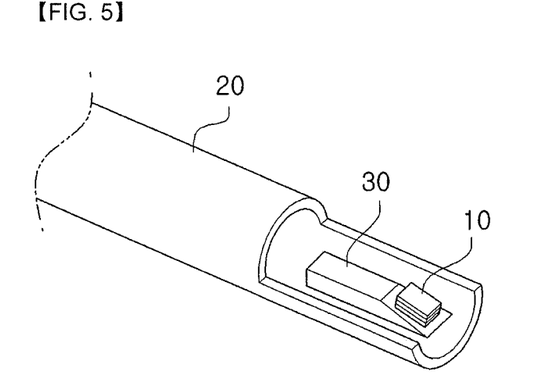
FIG. 5 is a perspective view showing an exposed part of the intravascular ultrasonic transducer structure of FIG. 3 according to another embodiment of the present disclosure.

FIG. 5 is a perspective view showing an exposed part of the intravascular ultrasonic transducer structure of FIG. 3 according to another embodiment of the present disclosure.

As described previously, it is shown that the single element ultrasonic transducer 10 is located at the end of the tube 20 such that it is fixed and arranged at a slant by the support 30. Through this structure, both the wall surface of the blood vessel into which the tube 20 is inserted and the traveling direction of the tube can be simultaneously observed, and the support of which the angle is freely adjusted according to the need can be used. Particularly, when this slant is used, advantages are that images can be obtained not only when the tube 20 goes backward but also when the tube 20 goes forward (is inserted), and a Doppler (blood flow velocity) can be measured.

Figure 6:
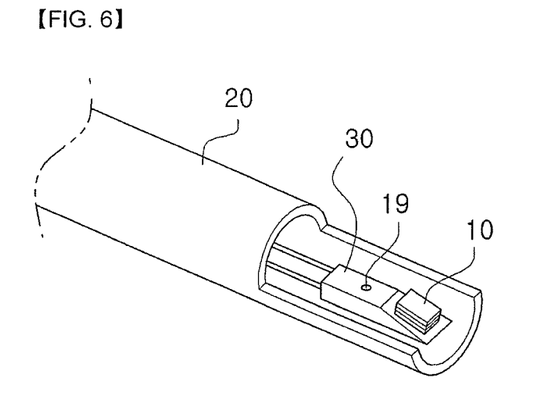
FIG. 6 is a diagram illustrating an example of a method for photoacoustic or optical coherence tomography (OCT) imaging in the intravascular ultrasonic transducer structure of FIG. 3 according to another embodiment of the present disclosure.

FIG. 6 is a diagram illustrating an example of a method for photoacoustic or optical coherence tomography (OCT) imaging in the intravascular ultrasonic transducer structure of FIG. 3 according to another embodiment of the present disclosure.

Photoacoustic (PA) imaging involves applying photons to an observation region in the human body, receiving ultrasonic signals directly generated by the photons absorbed into the tissues, and extracting image information from the signals. This unique situation in which ultrasonic waves are generated by absorption of photons in the tissues is a phenomenon appearing because the tissues are heated when absorbing photons, and when an absorbent tissue structure is irradiated by a pulsed laser, the temperature of the tissues changes, and as a result, the structure of the tissues expands. From this expanding structure, pressure waves propagate outside, and these pressure waves may be detected by the ultrasonic transducer. Accordingly, photoacoustic and ultrasound may share their configuration in certain parts (detecting/receiving).

To this end, in the ultrasonic transducer structure proposed in FIG. 6, the ultrasonic transducer 10 may further include an optical source module (not shown) which is inserted into a certain region 19 of the ultrasonic transducer 10 to emit optical signals for photoacoustic imaging. That is, by forming a hole in the ultrasonic transducer 10 and inserting an optical source module, an ultrasonic image as well as a photoacoustic image can be obtained. In addition, the optical source module can be also used to obtain an optical coherence tomography image, and through this, ultrasonic and optical coherence tomography fusion images of blood vessel diseases can be obtained.

Figure 7:
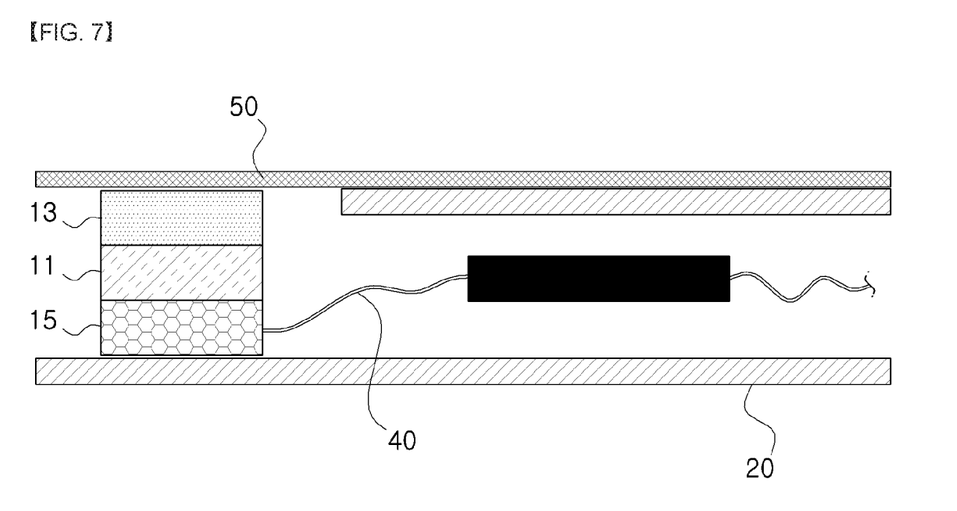
FIG. 7 is a diagram illustrating an example of a method for signal supply and grounding in the intravascular ultrasonic transducer structure of FIG. 3 according to another embodiment of the present disclosure.

FIG. 7 is a diagram illustrating an example of a method for signal supply and grounding in the intravascular ultrasonic transducer structure of FIG. 3 according to another embodiment of the present disclosure, and in the ultrasonic transducer structure proposed by the embodiments of the present disclosure, an electrical signal is supplied to the backing layer 15, and ground is created by connecting a housing 50 to the matching layer 13.

Referring to FIG. 7, a wire 40 is connected to the conductive backing layer 15 part by using a conductive adhesive to supply a signal, and ground is created by connecting the housing 50 and the conductive matching layer 13 through chrome or gold deposition. Of course, the configuration of FIG. 7 is just an example, and the conductive backing layer 15 may be connected to the housing material by depositing chrome/gold, and the conductive matching layer 13 may be connected to a wire. Also, in connecting to the housing material, a wire may be used, and connection may be also established by depositing materials other than chrome/gold.

On the other hand, it is hereinafter intended to propose another IVUS transducer production technology, including making each material that forms an IVUS ultrasonic transducer at a desired thickness using FPCB first, and then, performing matching and dicing to produce a plurality of individual IVUS transducers at the same time.

Figure 8:
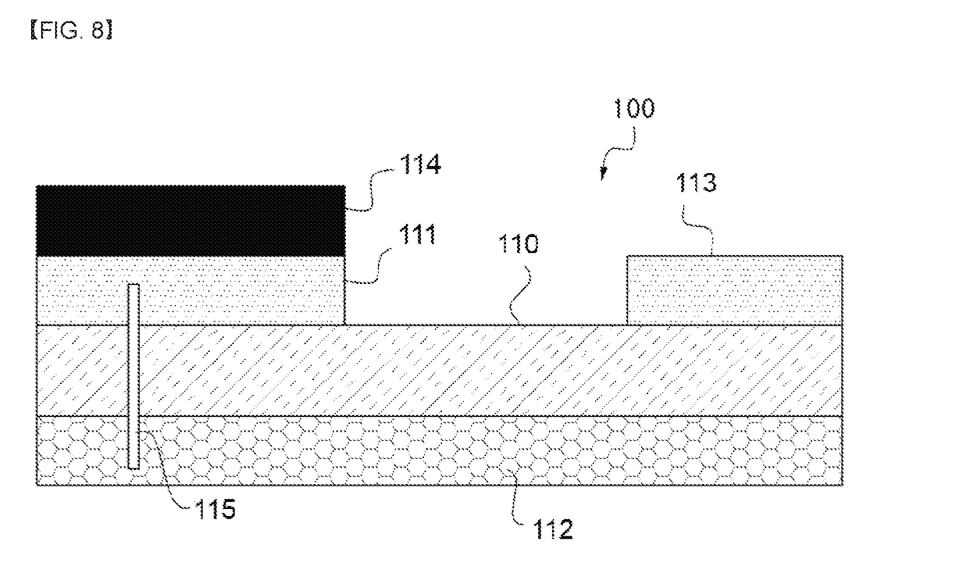
FIG. 8 is a cross-sectional view showing another embodiment of an ultrasonic transducer of a single element in the intravascular ultrasonic transducer structure of FIG. 3.

FIG. 8 is a cross-sectional view showing another embodiment of an ultrasonic transducer of a single element in the intravascular ultrasonic transducer structure of FIG. 3, including two signal pads 111, 112, a ground pad 113 and a piezoelectric material 114 with respect to a flexible printed circuit board (FPCB) 110.

The first signal pad 111 is formed on an upper surface of the FPCB 110, the second signal pad 112 is formed on a lower surface of the FPCB 110, the first signal pad 111 and the second signal pad 112 are electrically connected through at least one via 115 which passes through the FPCB 110.

The ground pad 113 is located on the upper surface of the FPCB 110 made of polyimide, and is spaced apart from the first signal pad 111.

The piezoelectric material 114 is lapped according to a preset thickness and is formed on an upper surface of the first signal pad 111. Also, a conductive material may be deposited on the upper surface of the FPCB 110 to connect the piezoelectric material 114 to the ground pad 113, and the conductive material may be chrome or gold, but is not limited thereto.

Bulk material 100 consisting of a stack of the piezoelectric material 114, the first signal pad 111, the ground pad 113, the FPCB 110 and the second signal pad 112 is diced along the stack direction to produce single elements which are less than or equal to a threshold size for intravascular ultrasound (IVUS). For example, the threshold size may be determined to be less than or equal to 1 mm×1 mm that is at least smaller than the cross section of the blood vessel.

When the FPCB is used as above, there are advantages; signal supply and grounding is accomplished through the signal and ground pads located on the FPCB with no need to use a conductive material for both the backing layer and the matching layer to facilitate signal supply and grounding in the same way as a conventional process, the backing layer (not shown) may match a lower surface of the second signal pad 112 and the matching layer (not shown) may match an upper surface of the piezoelectric material 114, and an ultrasonic transducer can be produced while not limiting the matching layer and the backing layer to a conductive material. That is, there is no limitation, whether conductive materials or non-conductive materials. Thus, in the case of this embodiment, as the process technology can obtain best transducer performance as described previously, it is advantageous for realizing high frequency characteristics of an IVUS transducer.

Figure 9A:
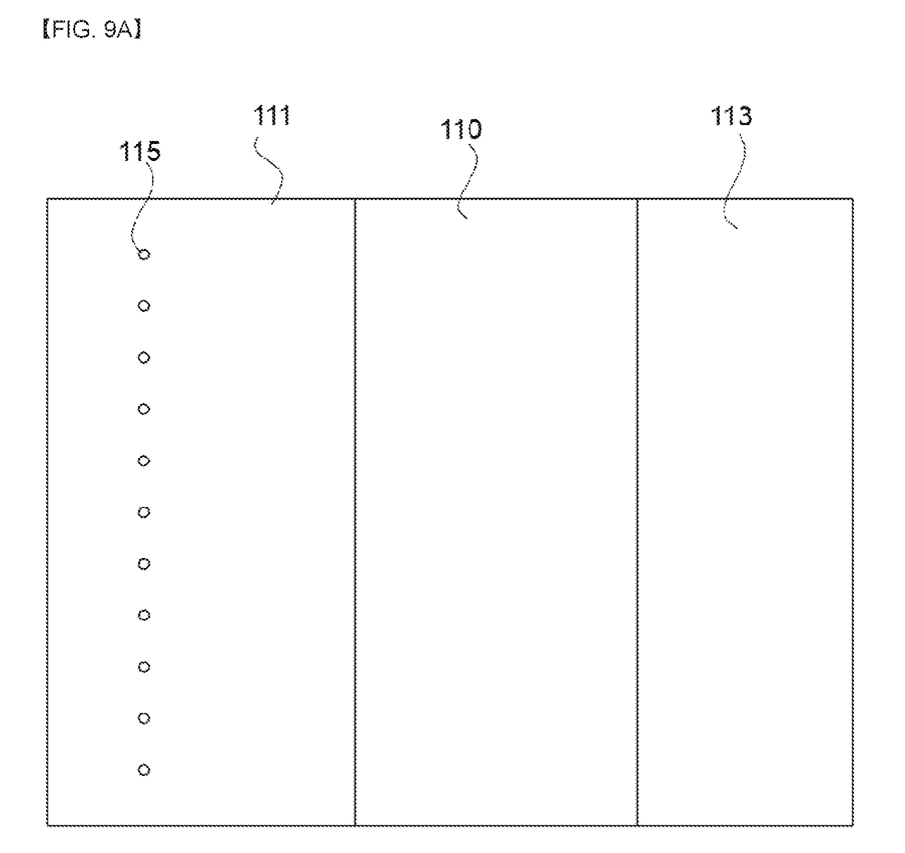
FIGS. 9A and 9B are plane views illustrating the intravascular ultrasonic transducer of FIG. 8 as viewed from top according to the producing process.
Figure 9B:
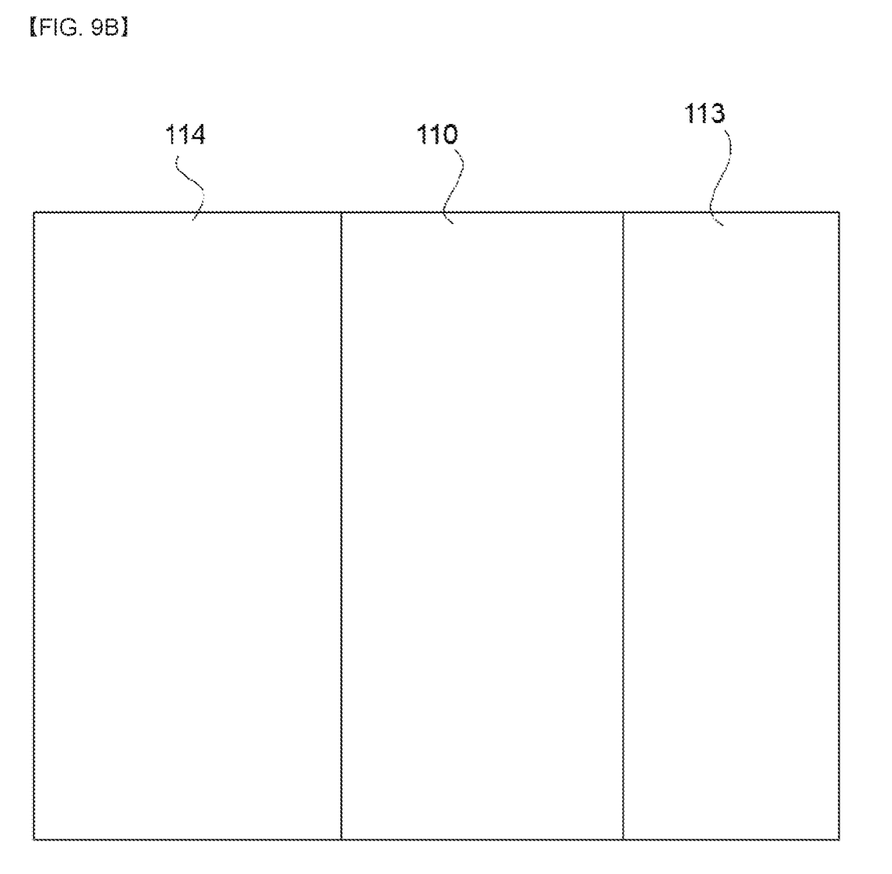

FIGS. 9A and 9B are plane views illustrating the intravascular ultrasonic transducer of FIG. 8 as viewed from top according to the producing process.

In FIG. 9A, it is assumed that the first signal pad 111 and the ground pad 113 are formed spaced apart from each other on the upper surface of the FPCB 110, and the second signal pad (not shown) is formed on the lower surface of the FPCB 120. Under this circumstance, it is shown that a via 115 hole for connecting the first signal pad 111 and the second signal pad (not shown) is formed to electrically connect the two (first signal pad and second signal pad). FIG. 9B shows that subsequent to the process of FIG. 9A, the piezoelectric material 114 is formed on the first signal pad.

Figure 9C:
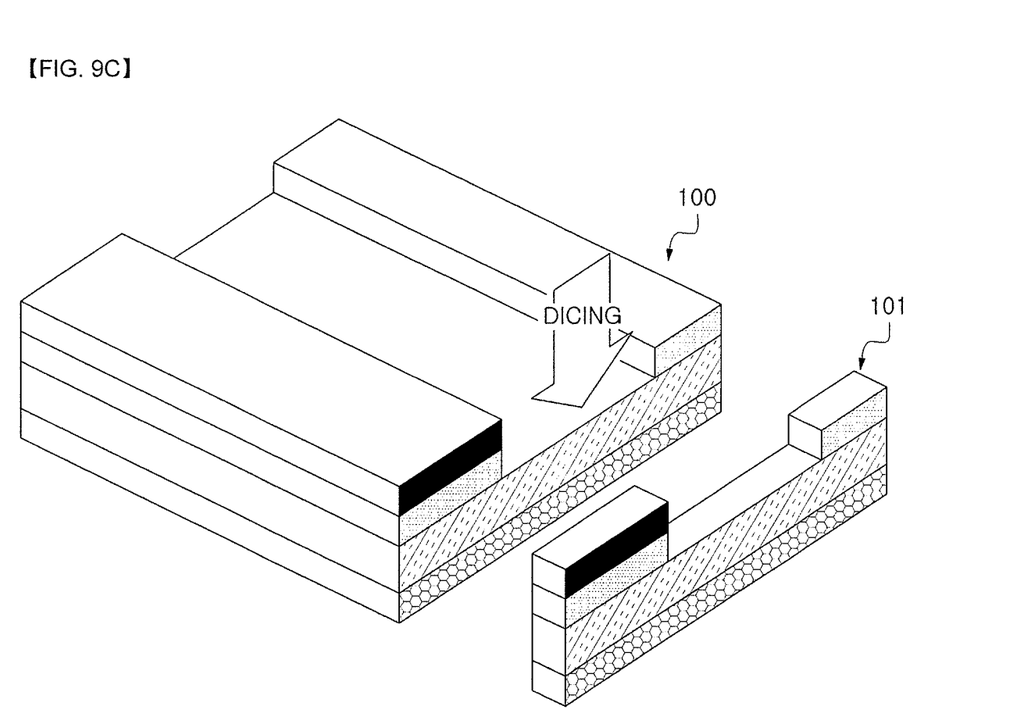
FIG. 9C is a diagram illustrating a method for producing a single element by dicing a stacked ultrasonic transducer, as the last stage of the producing process of FIGS. 9A and 9B.

FIG. 9C is a diagram illustrating a method for producing a single element by dicing a stacked ultrasonic transducer, as the last stage of the producing process of FIGS. 9A and 9B, and the stacked ultrasonic transducer 100 is diced perpendicular to the plane along the stack direction to consecutively produce a plurality of single elements 101. The IVUS ultrasonic transducer using FPCB as produced in this way can be now used as the ultrasonic transducer shown in FIGS. 3 through 7 as introduced previously.

Hereinabove the present disclosure has been described with respect to a variety of embodiments. Those skilled in the art will appreciate that the present disclosure may be embodied in modified form without departing from the essential features of the present disclosure. Therefore, the disclosed embodiments should be considered in illustrative aspects, not limitative aspects. The scope of the present disclosure is defined in the appended claims, not in the foregoing description, and all differences within the equivalent scope of the claims should be construed as being included in the present disclosure.

INDUSTRIAL APPLICABILITY

According to the embodiments of the present disclosure described above, by proposing process technology for the simultaneous production of a plurality of individual single element IVUS ultrasonic transducers through dicing after deposition and stacking of various types of elements, advantages are that an ultrasonic transducer which has a high operating frequency and an ultramicro aperture size and ensures economical efficiency can be produced without an adhesive, and beam convergence through a geometrical focus can be accomplished.

The invention claimed is:

1. An ultrasonic transducer structure comprising:
a tube for insertion into a blood vessel for intravascular ultrasound (IVUS);
an ultrasonic transducer of a single element consisting of a stack comprising a matching layer, a piezoelectric material, and a backing layer, wherein the ultrasonic transducer is installed at an open end of the tube to obtain an ultrasonic image;
wherein the stack comprises, in sequence, the piezoelectric material, a first signal pad, a ground pad formed spaced apart from the first signal pad, a flexible printed circuit board (FPCB), and a second signal pad electrically connected to the first signal pad through a via penetrating the FPCB, and
a support positioned between one side wall of the tube and the ultrasonic transducer, the support having a surface in contact with the ultrasonic transducer that is angled relative to the longitudinal direction of the tube to form an angle at which the ultrasonic transducer is oriented, and to adjust the angle to make an ultrasonic radiation angle of the ultrasonic transducer different from an insertion angle of the tube.

2. The ultrasonic transducer structure according to claim 1, wherein the angle at which the ultrasonic transducer is oriented by the support is determined to range between 0° and 90° from an insertion direction of the tube, to simultaneously obtain ultrasonic images of the insertion direction of the tube and a wall surface of the blood vessel into which the tube is inserted, or to estimate a Doppler frequency and calculate a blood flow velocity.

3. The ultrasonic transducer structure according to claim 1, wherein the ultrasonic transducer is formed in rectangular shape,
a length of a short side of the ultrasonic transducer is at least less than or equal to a diameter of the tube, and a length of a long side of the ultrasonic transducer is larger than or equal to the diameter of the tube, and
the long side of the ultrasonic transducer is inserted along an inner wall surface of the tube.

4. The ultrasonic transducer structure according to claim 1, wherein the end of the tube at which the ultrasonic transducer is installed has a cutting plane forming a slant in consideration of the ultrasonic radiation direction of the ultrasonic transducer.

5. The ultrasonic transducer structure according to claim 1, wherein the ultrasonic transducer forms a gradient such that a center surface is concave, to converge a beam to a geometrical focus of the ultrasonic transducer.

6. The ultrasonic transducer structure according to claim 1, wherein the ultrasonic transducer further comprises a convex lens attached to a front surface, to converge a beam to a geometrical focus of the ultrasonic transducer.

7. The ultrasonic transducer structure according to claim 1, wherein the ultrasonic transducer further comprises an optical source module which is inserted into a certain region of the ultrasonic transducer to emit an optical signal for photoacoustic imaging or optical coherence tomography (OCT) imaging.

8. The ultrasonic transducer structure according to claim 1, wherein an electrical signal is supplied to the backing layer, and ground is created by connecting a housing to the matching layer.

9. The ultrasonic transducer structure according to claim 1, wherein the ultrasonic transducer is produced as a single element by forming a piezoelectric material lapped according to a preset thickness,
depositing a conductive material on a lapped surface of the piezoelectric material,
casting a front surface and a rear surface of the piezoelectric material having the deposited conductive material to respectively form a matching layer and a backing layer and lapping according to a preset thickness, and
dicing the bulk material consisting of a stack of the matching layer, the piezoelectric material and the backing layer along a stack direction to allow insertion into the tube.

10. A method for producing an ultrasonic transducer according to claim 1, comprising:
forming a piezoelectric material lapped according to a preset thickness;
depositing a conductive material on a lapped surface of the piezoelectric material;
casting a front surface and a rear surface of the piezoelectric material having the deposited conductive material to respectively form a matching layer and a backing layer and lapping according to a preset thickness; and
dicing the bulk material with a stack of the matching layer, the piezoelectric material and the backing layer along a stack direction to produce single elements which are less than or equal to a threshold size for intravascular ultrasound (IVUS).

11. The method for producing an ultrasonic transducer according to claim 10, wherein the matching layer and the backing layer are formed directly on the conductive material through the casting without using an adhesive material.

12. The method for producing an ultrasonic transducer according to claim 10, wherein the matching layer and the backing layer are cured using a centrifugal separator after the casting.

13. The method for producing an ultrasonic transducer according to claim 10, wherein the conductive material is chrome or gold.

14. An ultrasonic transducer structure, comprising:
a tube for insertion into a blood vessel for intravascular ultrasound (IVUS);
an ultrasonic transducer of a single element consisting of a stack comprising a matching layer, a piezoelectric material, and a backing layer, wherein the ultrasonic transducer is installed at an end of the tube to obtain an ultrasonic image; and
a support positioned between one side wall of the tube and the ultrasonic transducer to form an angle at which the ultrasonic transducer is oriented, and to adjust the angle to make an ultrasonic radiation angle of the ultrasonic transducer different from an insertion angle of the tube,
wherein the stack comprises, in sequence, the piezoelectric material, a first signal pad, a ground pad formed spaced apart from the first signal pad, a flexible printed circuit board (FPCB), and a second signal pad electrically connected to the first signal pad through a via penetrating the FPCB,
the backing layer is lapped according to a preset thickness and is formed on a lower surface of the second signal pad, and
after the matching layer electrically connects an upper surface of the piezoelectric material and the ground pad, the matching layer is lapped according to a preset thickness and is formed on the upper surface of the piezoelectric material.

15. The ultrasonic transducer structure according to claim 14, wherein a conductive material is deposited on an upper surface of the FPCB to connect the piezoelectric material to the ground pad.

16. The ultrasonic transducer structure according to claim 14, wherein the FPCB is polyimide.

17. The ultrasonic transducer structure according to claim 14, wherein the ultrasonic transducer is formed in rectangular shape,
a length of a short side of the ultrasonic transducer is at least less than or equal to a diameter of the tube, and a length of a long side of the ultrasonic transducer is larger than or equal to the diameter of the tube, and
the long side of the ultrasonic transducer is inserted along an inner wall surface of the tube.

18. The ultrasonic transducer structure according to claim 14, wherein the ultrasonic transducer forms a gradient such that a center surface is concave, to converge a beam to a geometrical focus of the ultrasonic transducer.

19. The ultrasonic transducer structure according to claim 14, wherein the ultrasonic transducer further comprises an optical source module which is inserted into a certain region of the ultrasonic transducer to emit an optical signal for photoacoustic imaging or optical coherence tomography (OCT) imaging.

* * * * *